(12) United States Patent
Bufala et al.

(10) Patent No.: US 7,959,944 B2
(45) Date of Patent: Jun. 14, 2011

(54) S-ADENOSYL-L-METHIONINE FOR REGULATING BEHAVIORAL DISORDERS IN PETS

(75) Inventors: Georges Bufala, Antibes (FR); Christophe Reme, Nice (FR)

(73) Assignee: Virbac, Carros (FR)

( * ) Notice: Subject to any disclaimer, the term of this patent is extended or adjusted under 35 U.S.C. 154(b) by 688 days.

(21) Appl. No.: 11/918,379

(22) PCT Filed: Apr. 14, 2006

(86) PCT No.: PCT/EP2006/061619
§ 371 (c)(1),
(2), (4) Date: Oct. 12, 2007

(87) PCT Pub. No.: WO2006/108880
PCT Pub. Date: Oct. 19, 2006

(65) Prior Publication Data
US 2008/0199520 A1 Aug. 21, 2008

(30) Foreign Application Priority Data
Apr. 15, 2005 (FR) ..................... 05 03782

(51) Int. Cl.
*A23K 1/17* (2006.01)
*A01N 43/04* (2006.01)
*A61K 31/70* (2006.01)

(52) U.S. Cl. ......................... 424/442; 514/46
(58) Field of Classification Search .......... None
See application file for complete search history.

(56) References Cited

U.S. PATENT DOCUMENTS

| | | | |
|---|---|---|---|
| 3,954,726 A | 5/1976 | Fiecchi | |
| 4,057,686 A | 11/1977 | Fiecchi | |
| 4,369,177 A | 1/1983 | Kozaki et al. | |
| 4,956,173 A | 9/1990 | Le Fur et al. | |
| 5,073,546 A | 12/1991 | Zappia et al. | |
| 5,753,213 A | 5/1998 | Moratti | |
| 5,776,911 A | 7/1998 | Szabo | |
| 6,093,703 A | 7/2000 | La Greca | |
| 6,914,071 B2 * | 7/2005 | Zicker et al. | 514/440 |
| 2005/0014698 A1 * | 1/2005 | Friesen et al. | 514/18 |

FOREIGN PATENT DOCUMENTS

| | | |
|---|---|---|
| EP | 0 191 133 | 11/1989 |
| EP | 0 473 252 | 3/1997 |
| EP | 0 623 344 | 7/2000 |
| EP | 1 050 303 | 11/2000 |
| FR | 2 823 211 | 10/2002 |
| FR | 05 03782 | * 4/2005 |
| WO | WO 01/21178 | 3/2001 |
| WO | WO 01/85165 | 11/2001 |
| WO | WO 02/32434 | 4/2002 |
| WO | WO 02/45525 | 6/2002 |
| WO | WO 2005/006877 | 1/2005 |

OTHER PUBLICATIONS

Michell. "Longevity of British breeds of dogs and its relationship with sex, size, cardiovascular variable and diseases". *The Veterinary Record*, vol. 145, pp. 625-629 (Nov. 27, 1999).
Barette. "Feeding older cats and dogs." *Can. Vet. J.*, vol. 31, pp. 784-785 (Nov. 1990).
Taylor et al. "Some nutritional aspects of ageing in dogs and cats" *Proc. Nutr. Soc.*, vol. 54, pp. 645-656 (1995).
Friedel et al. "S-Adenosyl-L-Methionine A review of its Pharmacological Properties and Therapeutic Potential in Liver Dysfunction and Affective Disorders in Relation to its Physiological Rile in Cell Metabolism". *Drugs*, vol. 38 (3), pp. 389-416 (1989).
Freedom of Information Summary, Aniprul® tablets for use in dogs, NADA 148-080 (Dec. 10, 1998).
"Les traitements du comportement du chien et du chat". *Le Point Veterinaire*, vol. 35, pp. 5, 12-14, 36-39, 82-88, 114-115 (2004).
International Search Report for International Publication No. PCT/EP2006/061619 dated Jun. 12, 2006.
Landsberg ."Therapeutic agents for the treatment of cognitive dysfunction syndrome in senior dogs" *Progress in Neuro-Psychopharmacology & Biological Psychiatry*. vol. 29, No. 3, Mar. 2005 pp. 471-479.

* cited by examiner

*Primary Examiner* — Traviss C McIntosh, III
(74) *Attorney, Agent, or Firm* — Hamre, Schumann, Mueller & Larson, P.C.

(57) ABSTRACT

The present invention relates to the use of S-adenosyl-L-methionine or its salts for preparing a composition for the regulation of behavioral problems in pets.

13 Claims, 6 Drawing Sheets

Figure 1: Activity level of dogs
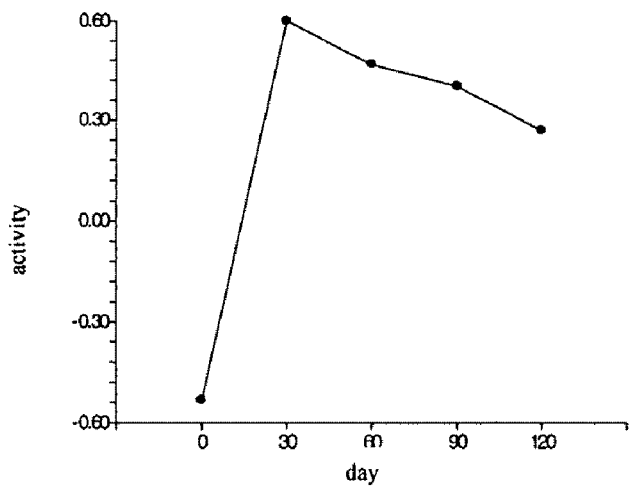
Activity level: −1 = reduced or visibly reduced, 0 = unchanged, 1 = increased
Figure 2: Sleeping time of dogs
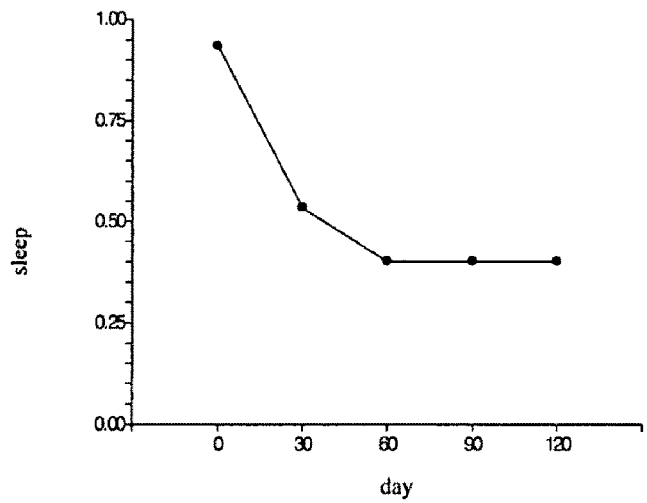
Sleeping time: 0 = unchanged, 2 = increased or reduced Figure 3: Anxiety of dogs
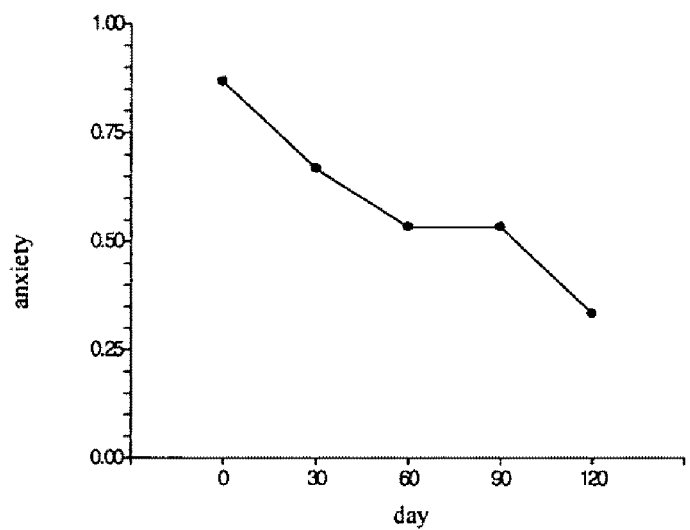
Anxious behavior: 0 = none, 1 = sporadic, 2 = frequent, 3 = permanent
Figure 4: Overall fear score
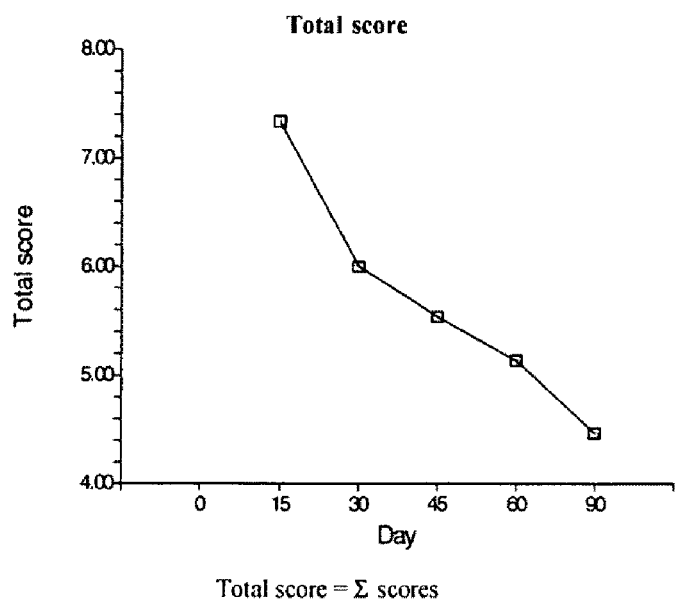
Total score = Σ scores

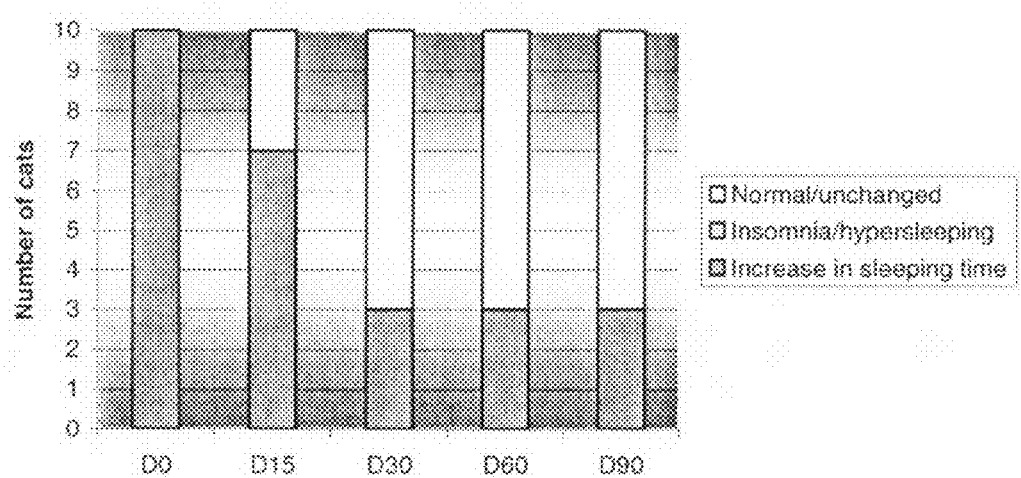
Figure 5: Wake-sleep cycle of cats
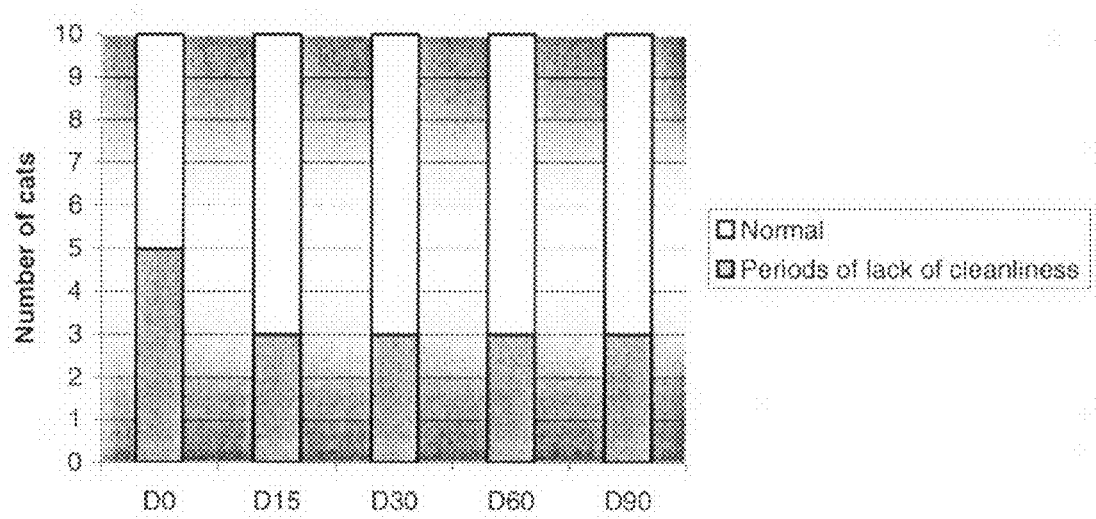
Figure 6: Elimination behavior of cats

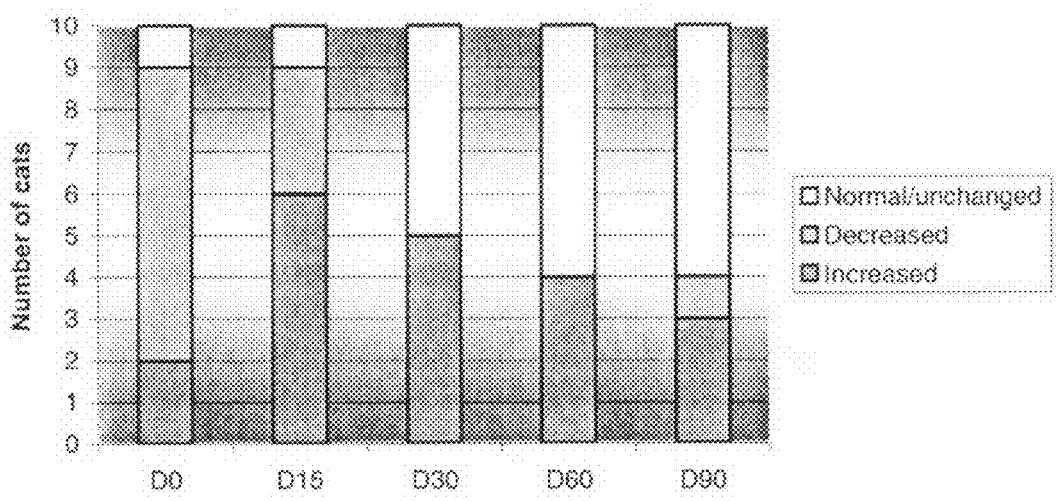
Figure 7: Exploratory behavior of cats
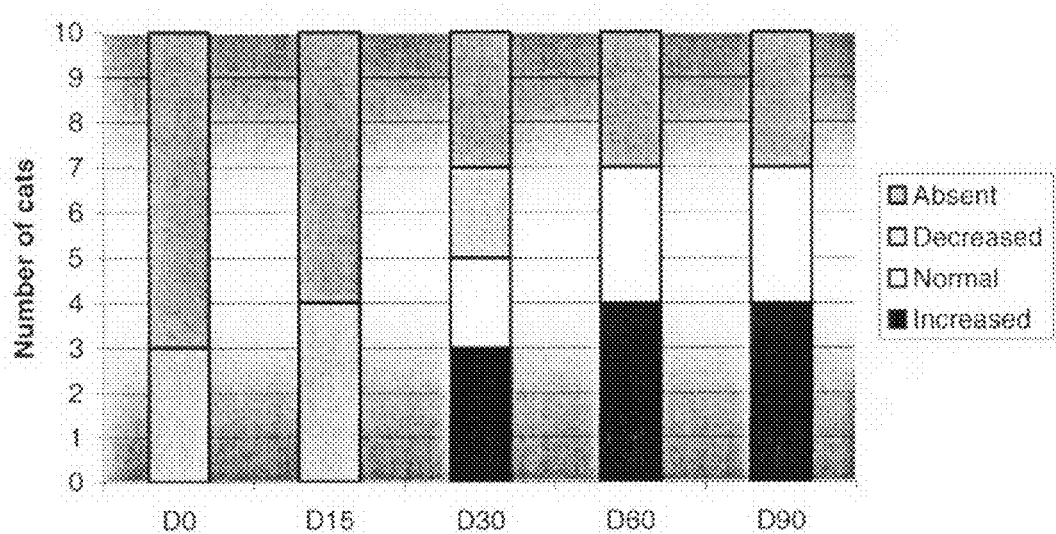
Figure 8: Play activity of cats Figure 9: Interactions/recognition (with/of the owners, other animals) by cats
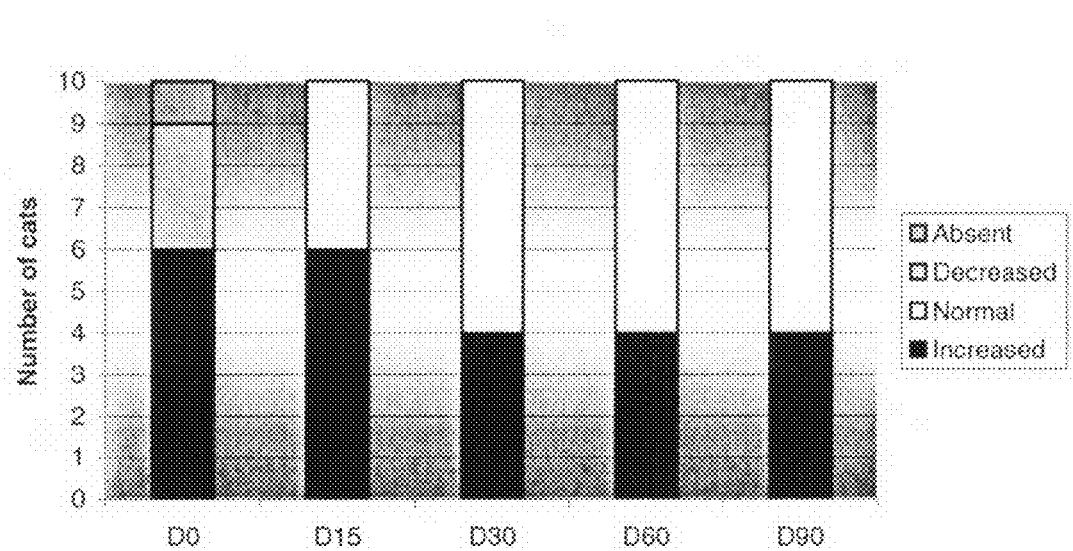
Note: increased = hyperattachment, separation anxiety
Figure 10: Aggressiveness, irritability of cats
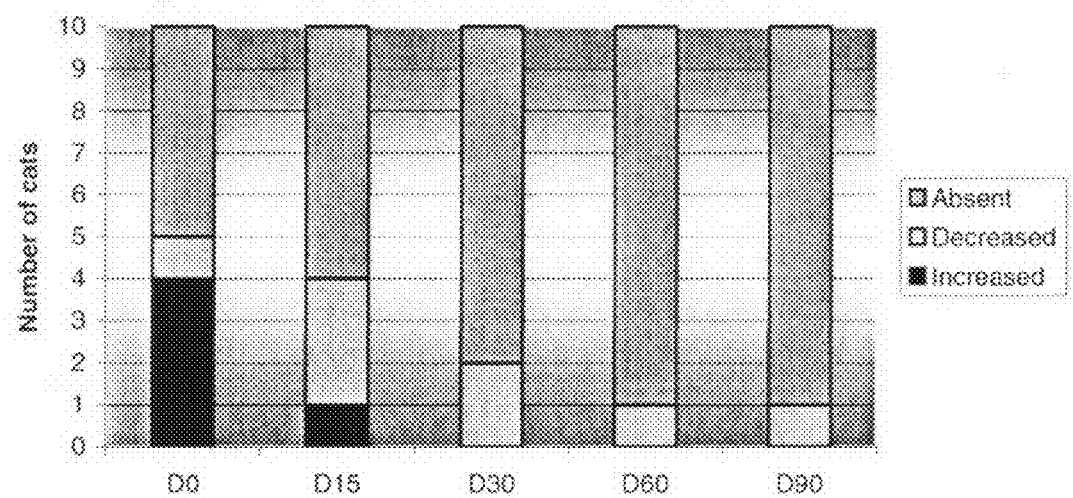

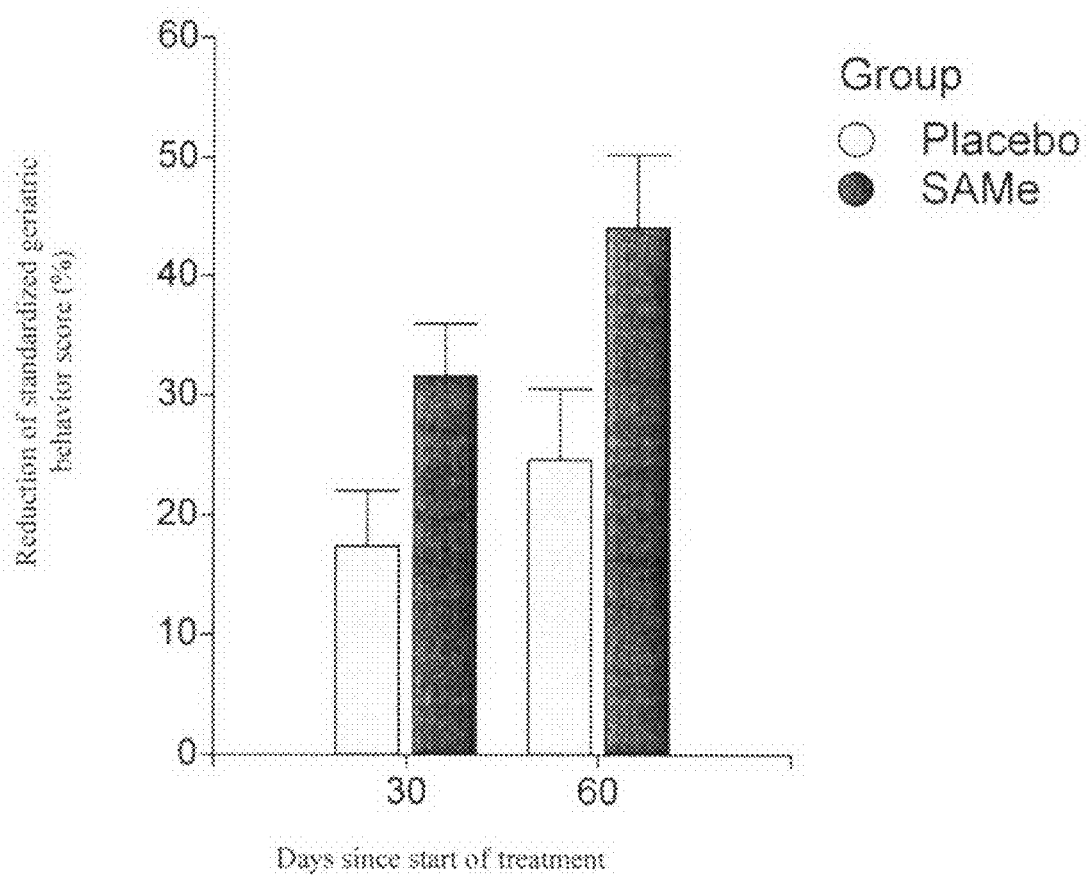

S-ADENOSYL-L-METHIONINE FOR REGULATING BEHAVIORAL DISORDERS IN PETS

The present invention relates to the use of S-adenosyl-L-methionine and its salts for carrying out a method of regulating behavioral problems in pets, especially behavioral changes related to age and particularly those associated with cognitive dysfunction syndrome (CDS). The invention further relates to the use of S-adenosyl-L-methionine or its pharmaceutically acceptable salts for preparing a drug for the prevention or treatment of cognitive dysfunction syndrome in pets, particularly dogs and cats.

Cognitive dysfunction syndrome (CDS) is an age-related behavioral disorder. It is observed in dogs and cats and is characterized by a deterioration of cognitive abilities (such as spatial orientation, contact with humans, learning, etc.); it is not attributed to motor or sensory dysfunctions or to general medical conditions such as neoplasias, infections or organic insufficiencies. In dogs, CDS is often referred to by veterinarians as "old dog syndrome" or simply "senility". In the absence of physical causes, it manifests itself by at least one of the following five behavioral changes:

disorientation/confusion;
decrease in or degradation of interaction (reactivity) with members of the owner's family;
perturbation of sleep-activity cycle;
decrease in activity level;
loss of cleanliness.

Similar symptoms can be observed in cats and the expression "feline cognitive dysfunction syndrome" is used.

The prevalence of cognitive dysfunction syndrome, e.g. in old dogs, is significant. A study of the subject has shown that 62% of dogs aged between 11 and 16 years fall in one or more of the behavioral categories characteristic of CDS.

The causes of CDS are not really known. Studies have shown that the behavioral changes associated with this syndrome increase with age and that numerous pathological changes that appear in old dogs and cats are capable of causing CDS.

Identification of the behavioral changes that are directly and uniquely associated with CDS in pets is relatively difficult for the practitioner because it is based on an "exclusion" procedure. In fact, behavioral changes identical to those directly associated with CDS are symptomatic of many diseases. Thus the veterinary practitioner can only decide in favor of CDS if he has not diagnosed other pathological conditions with which the same behavioral symptoms are associated.

Examples of diseases that should not be confused with CDS and with which certain behavioral symptoms can be associated are listed below:

| Medical condition | Associated behavioral changes |
|---|---|
| Sensory dysfunction (loss of sight, hearing, smell) | Increase in irritability, fear or aggressiveness; decrease in appetite; increase in vocalizations; changes in wake-sleep cycle; disorientation; decrease in greeting behavior; inattentive, decrease in response to verbal orders |
| Urinary tract disease; renal disease | Incontinence, loss of cleanliness, polyuria, polyphagia |
| Arthrosis | Weak, reduced mobility or activity; irritability, possibility of inappropriate eliminations |
| Hypothyroidism | Decrease in activity, increase in irritability and aggressiveness |
| Deregulation of hypophyso-suprarenal axis (hypercorticism) | Polyphagia, polyuria, decrease in social interaction, responses to orders and greeting behavior; reduction in activity; loss of cleanliness; perturbation of wake-sleep cycle |
| Neurological disorders (primary and secondary intracranial neoplasia) | Change in wake-sleep cycle, eating habits, cleanliness, aggressiveness and docility |

Whatever its causes, CDS, just like the diseases with which the same behavioral symptoms are associated, can dramatically affect an animal's health and well-being. Consequently, the company of a dog or cat suffering from CDS can rapidly become less pleasant, or even difficult to tolerate, especially if the severity of the associated behavioral changes, such as depression, anxiety, aggressiveness or lack of cleanliness, increases. In extreme cases, euthanasia of the animal may be envisaged.

It is difficult to specify the longevity of an individual dog, but it is not rare to find dogs that proudly reach an age of fifteen years or more. If an average age has to be specified (considering all breeds together), it is about twelve years taking into account all the parameters, especially premature mortality (at about eight years) due to cancers and heart problems. A study conducted in England establishes that the average age at the time of death, considering all causes together, varies appreciably according to the breed in question. It is about 15 years for the toy poodle, 13 years for the Dalmatian, fox terrier or Chihuahua and only a little over 4 years for the Saint Bernard (MICHELL A.-R., Longevity of British breeds of dogs and its relationship with sex, size, cardiovascular variable and diseases. The Veterinary Record (1999) 145, 625-629). There is also some variability between breed of cats as regards their longevity. At the present time the average life expectancy of a pet cat is 14 years and the record is 36 years (BARETTE D. Feeding older cats and dogs. Can. Vet. J., 1990, 31, 784-785; TAYLOR E. J., ADAMS C., NEVILLE R. Some nutritional aspects of ageing in dogs and cats. Proc. Nutr. Soc., 1995, 54, 645-656). A cat is generally considered to be old beyond 9 or 10 years.

Given the increased life expectancy of dogs and cats, due especially to the improvement in veterinary care, nutrition and accidental death prevention, age-related behavioral changes in pets have become a problem of major interest. In addition to the behavioral changes already mentioned above, there may also be mentioned the modifications in the animal's food intake, the modifications in licking and grooming behavior or else the increase in aggressiveness and irritability. This led the Applicant to search for means of regulating behavioral disorders in pets, but also methods of preventing the appearance of behavioral changes, particularly those associated with CDS, as well as increasingly effective drugs for the prevention and treatment of behavioral disorders, particularly those related to age and more particularly behavioral changes associated with CDS.

Thus, cognitive dysfunction syndrome in dogs is now recognized as a disease in the United States by the regulatory authorities in charge of drug registration since this body granted a therapeutic indication to a drug based on selegiline hydrochloride for controlling the clinical signs associated with cognitive dysfunction syndrome in dogs (Freedom of Information Summary, Anipryl® Tablets for use in dogs, NADA, 141-080).

Furthermore, intensive research on the subject has led in recent years to the filing of several patent applications relating to novel pharmaceutical compositions. EP patent 0 623 344, for example, relates to the use of selegiline hydrochloride for the treatment of behavioral disorders in dogs or cats. EP patent 1 050 303 in turn describes the use of acetylcholinesterase inhibitor for the treatment of age-related behavioral disorders in pets, including cognitive dysfunction syndrome. Also, WO patent application 01/21178 describes the use of a composition containing an effective amount of propentofylline for the treatment of cognitive dysfunction syndrome in dogs, and EP patent 0 473 252 describes the use of the compound L-deprenyl for delaying age-related deterioration in dogs, especially deterioration of the cognitive functions.

The 2004 special issue (volume 35) of the journal "Le Point Vétérinaire", entitled "Les traitements du comportement du chien et du chat" ("Treatments of canine and feline behavior"), reviews treatments in veterinary behavioral medicine, dealing with all the facets of the specialized branch, from chemotherapy to behavioral therapy, from neurophysiological bases to ecological interventions, and from surgery to pheromone therapy. Some articles in this review draw up an exhaustive list of the different biological treatments currently used in age-related behavioral disorders. They mention especially monoamine oxidase inhibitors (MAOI) such as selegiline, tricyclic antidepressants such as clomipramine, selective serotonin reuptake inhibitors (SSRI) such as fluoxetine and fluvoxamine, morpholines such as trioxazine, and other molecules such as piracetam, adrafinil, propentofylline, nicergoline and vincamine.

The article by Gary Landsberg (Therapeutic agents for the treatment of cognitive dysfunction syndrome in senior dogs, Progress in Neuro-Psychopharmacology & Biological Psychiatry, 29 (2005) 471-479) also lists a number of treatments currently used, or capable of being envisaged, to combat this syndrome.

In the course of its own research studies, the Applicant has found, surprisingly, that the administration of a composition based on S-adenosyl-L-methionine, or one of its salts, to a pet presenting one or more behavioral changes related to age, particularly those associated with cognitive dysfunction syndrome, makes it possible to reduce the intensity of these behavioral changes or even to restore the animal's behavior to normal.

S-adenosyl-L-methionine, or 5'-[[3S-amino-3-carboxypropyl]methyl-(S)-sulfonio]-5'-deoxyadenosine, which is abbreviated to SAM or SAMe, is a natural metabolite of methionine. This molecule is present in all the tissues of living organisms and participates in a very large number of biochemical processes. In particular, it acts as a donor of methyl groups in a substantial number of transmethylations, and as a precursor in the synthesis of sulfur compounds such as glutathion, cysteine, taurine and coenzyme A.

In the organism SAMe is produced from L-methionine and ATP by methionine adenosyltransferase. It is therefore possible to increase the tissue levels of SAMe by administering copious doses of exogenous L-methionine. However, methionine seems to be toxic at high doses, which is not the case for SAMe. Nevertheless, SAMe is an unstable compound which is rapidly degraded on contact with air and moisture, making it difficult to use. A small amount of SAMe is present in food, but, due to its instability, this means of supplying the organism with SAMe is negligible.

There are numerous publications dealing with the different biological actions of SAMe, and several patents describe SAMe, its activities, its salts, their properties and their uses. In this regard, reference may be made in particular to patents U.S. Pat. No. 3,954,726, U.S. Pat. No. 4,057,686, U.S. Pat. No. 4,369,177, EP 0 191 133 B1, U.S. Pat. No. 4,956,173, U.S. Pat. No. 5,073,546, U.S. Pat. No. 5,753,213, U.S. Pat. No. 5,776,911, U.S. Pat. No. 6,093,703, FR 2 823 211 and WO 02/32434 and to the article by Friedel et al. in DRUGS (1989), 38(3), 389-416.

It will be noted in particular that SAMe is cited among the sulfur-containing antioxidants that can be used in the pet foods described in international patent applications WO 02/45525 and WO 2005/006877 for the purpose of inhibiting and/or reducing mental deterioration in pets, optionally in combination with other antioxidants or omega-3 fatty acids (WO 2005/006877). Said documents neither demonstrate nor suggest that SAMe alone can have properties for regulating behavioral problems in pets.

SAMe and its salts have numerous therapeutic and non-therapeutic applications, but their use for regulating behavioral problems in pets, especially behavioral changes related to age and particularly those associated with cognitive dysfunction syndrome, has never been described or suggested.

Thus the present invention relates to the use of S-adenosyl-L-methionine or one of its salts for preparing a composition for regulating behavioral problems in pets, preferably dogs and particularly preferably cats.

The composition is preferably a drug or a nutritional supplement.

The pet is preferably a cat.

The behavioral problems which the Applicant proposes to regulate are behavioral changes that are most often related to age or associated with cognitive dysfunction syndrome.

According to another aspect, the invention further relates to a method of preventing or delaying the appearance of at least one age-related behavioral change in pets, or a method of treating cognitive dysfunction syndrome in pets, which consists in the regular administration of an effective amount of S-adenosyl-L-methionine to the pets.

The age-related behavioral changes mentioned above are behavioral changes that are not associated with a specific pathological condition, particular examples being disorientation/confusion; decrease in or degradation of interaction (reactivity) with members of the owner's family; perturbation of sleep-activity cycle; decrease in activity level; and loss of cleanliness.

The method of treatment according to the invention can be used to treat any old pets, particularly dogs and cats and especially senior dogs and cats.

The S-adenosyl-L-methionine salts which are suitable for the purposes of the present invention are the salts with organic or inorganic acids, particularly the pharmaceutically acceptable salts. Non-limiting examples which may be mentioned are the salts of SAMe with hydrochloric acid, sulfuric acid, p-toluenesulfonic acid, formic acid, acetic acid, citric acid, tartaric acid, maleic acid and 1,4-butane-disulfonic acid, and the double salts of SAMe with the above acids.

Preferably, the S-adenosyl-L-methionine salts according to the invention are the salts of SAMe with p-toluenesulfonic acid and 1,4-butanedisulfonic acid.

According to the invention, the composition is preferably adapted for administration by the enteral route, particularly the oral route, in which case it can take the form of a divisible or indivisible tablet, a divisible or indivisible chewable tablet, a capsule, a bolus, a powder, granules, a solution or suspension to be taken orally, or a paste. The pharmaceutical composition can also be administered by the parenteral route.

The composition according to the invention will be prepared in conventional manner with the excipients commonly used in the food and/or veterinary sector to give such solid, liquid or pasty compositions. Preferably, an appropriate excipient will be chosen to guarantee the stability of the SAMe, examples being paraffin oil, liquid petrolatum, microcrystalline cellulose or magnesium stearate.

According to the invention, the composition can also comprise one or more substances selected e.g. from free radical inhibitors, anti-inflammatories, amino acids, trace elements in organic or inorganic form, vitamins and nutriments, this list not implying a limitation. It is advantageous to use magnesium and group B vitamins.

The drug according to the invention preferably comprises one or more additional active principles capable of enhancing and/or complementing the activity of the S-adenosyl-L-methionine and its pharmaceutically acceptable salts in its indication for cognitive dysfunction syndrome in pets. Examples of additional active principles which may be mentioned are selegiline hydrochloride, propentofylline, pentoxyfylline or L-deprenyl, this list not implying a limitation.

In one preferred embodiment of the invention, the drugs take the form of tablets, preferably divisible tablets that can be divided into two, four or more parts so that the dose of SAMe can be adjusted according to the weight of the animal to be treated or supplemented.

Advantageously, to ensure good keeping properties, the composition is protected from air and moisture, either by a film coating or ordinary coating, or by the packaging of the nutritional supplement or the drug, or else by a combination of the two, according to methods well known to those skilled in the art.

In another embodiment of the invention, the composition is adapted for the administration of a dose of S-adenosyl-L-methionine of between about 1 and about 50 mg per kg of body weight per day.

Particularly preferably, this composition is adapted for the administration of a dose of S-adenosyl-L-methionine of between about 2.5 and about 20 mg per kg of body weight per day, and very particularly preferably of between about 5 mg and about 10 mg per kg of body weight per day. Preferably, this composition is adapted for the administration of a dose of S-adenosyl-L-methionine of about 7 mg per kg of body weight per day.

In another preferred embodiment of the invention, the composition is administered once or twice a day, every day for a period of at least 15 days, preferably of at least 8 weeks and particularly preferably of at least 12 weeks or even 16 weeks. One variant may consist in administering the composition in an appropriate form, e.g. a sustained-action form, at a frequency ranging from one administration every two days to one administration a week. The period over which the nutritional supplement and/or pharmaceutical composition is taken can advantageously be prolonged to the end of the animal's life.

In the present description the expression "to regulate behavioral problems in pets, especially behavioral changes related to age and particularly those associated with cognitive dysfunction syndrome" means to reduce the severity of one or more behavioral changes, especially those related to age or associated with cognitive dysfunction syndrome, or else to prevent or delay the occurrence of one or more behavioral changes, especially those related to age or associated with cognitive dysfunction syndrome.

The expression "related to age" means resulting from non-pathological natural ageing processes. For pets, particularly dogs and cats, the expression "old animal" or "senior dog" or "senior cat" will be used when the animal has reached an age equivalent to 75% of the average longevity of the breed in question.

The expression "to prevent or delay signs of disorientation or confusion" means to reduce the pet's tendency e.g. to appear lost, wander aimlessly, vocalize without reason or stare into nowhere or at a wall.

The expression "to prevent or delay the degradation of social interactions" means to increase or re-establish a pet's tendency e.g. to crave the attention of members of the owner's family or greet the members of the family.

The expression "to prevent or delay perturbation of the sleep-activity cycle" means to increase or re-establish a pet's tendency to sleep at night, reduce or re-establish a pet's tendency to sleep during the day, or reduce a pet's tendency to wander or move about at any time during a 24-hour day.

The expression "to prevent or delay the loss of cleanliness" means e.g. to reduce the frequency with which the pet urinates or defecates inside the house, urinates or defecates inside the house in front of members of the owner's family, or urinates or defecates inside just after having gone out for a walk. For pets which are in the habit of indicating the wish to go out, these terms include an improvement in the frequency with which a pet asks to go out.

The expression "to prevent or delay the decrease in activity level" means to increase or re-establish a pet's tendency to move or play.

"Nutritional supplement" denotes any product, taking the form of a tablet, a capsule, a powder, a solution to be taken orally, a suspension to be taken orally, a paste or a gel for oral administration, or another medicinal form not usually associated with foods, which is intended to be ingested as a supplement to the normal diet in order to correct the actual or supposed deficiency of the daily intakes.

The invention will be better understood on reading the following description illustrating the unexpected properties of SAMe, particularly by way of Examples of the use of compositions based on SAMe or its salts for carrying out the invention.

It must be clearly understood, however, that these Examples are given solely by way of illustration of the invention and do not in any way imply a limitation.

FIG. 1 illustrates the change in the mean activity level of dogs receiving SAMe daily for 4 months. The following scores are applied to the animals: −1=activity level reduced or visibly reduced, 0=activity level unchanged, 1=activity level increased.

FIG. 2 illustrates the effect of the daily administration of SAMe for 4 months on the sleeping time of dogs. The following scores are applied to the animals: 0=sleeping time unchanged, 2=sleeping time increased or reduced.

FIG. 3 illustrates the effect of the daily administration of SAMe for 4 months on the anxiety of dogs. The following scores are applied to the animals. Anxious behavior: 0=none, 1=sporadic, 2=frequent, 3=permanent.

FIG. 4 illustrates the overall fear score in dogs, which is the sum of the scores of the following 6 parameters: pupil dilation, trembling, exploration, contact with humans, mood, drool/urine/defecation.

FIG. 5 illustrates the effect of the daily administration of SAMe for 3 months on the wake-sleep cycle of cats.

FIG. 6 illustrates the effect of the daily administration of SAMe for 3 months on the elimination behavior of cats, the periods of lack of cleanliness being recorded.

FIG. 7 illustrates the effect of the daily administration of SAMe for 3 months on the exploratory behavior of cats.

FIG. 8 illustrates the effect of the daily administration of SAMe for 3 months on the play activity of cats.

FIG. 9 illustrates the effect of the daily administration of SAMe for 3 months on the interactions of cats with the owners or other animals. In particular, the cats' recognition of the owners or other known animals is evaluated.

FIG. 10 illustrates the effect of the daily administration of SAMe for 3 months on the aggressiveness and/or irritability of cats, which, if it exists, manifests itself e.g. by the following signs: the pupils are dilated, the mouth is wide open, the cat pants, spits and shows its canines.

FIG. 11 illustrates the reduction of the "standardized geriatric behavior score" (sum of the scores of several behavioral disorders on a scale of 1 to 3) in dogs.

EXAMPLE 1

Materials and Method

A study was conducted to show the efficacy of S-adenosyl-L-methionine in old dogs presenting behavioral disorders associated with CDS.

S-adenosyl-L-methionine was administered in the form of tablets containing 10, 50 or 100 mg of SAMe.

15 dogs more than 7 years old were selected with no restrictions on breed, sex or weight. All the dogs presented well-established cognitive disorders associated with CDS (cleanliness problems, disorders of activity-sleep cycle, decrease in activity) which had been observed by their owners and by veterinarians.

Dogs presenting diseases requiring medical treatment were excluded from the study, as were dogs which had been treated with psychotropic drugs in the month preceding the study. Also, to avoid biases in the observations, heart, kidney and liver treatments and psychoactive drugs were not permitted during the study.

During the study the dogs received at least the equivalent of 2.5 mg of SAMe per kg of body weight per day in a single daily administration over a period of 4 months.

The dogs were examined by a veterinarian at the start of the experiment and then every month. The blood parameters were analyzed at each veterinary examination. The owners were also asked to give their opinion on the changes observed in the behavior of their pets.

Experiment number 1: Measurement of the activity level of the dogs. See FIG. 1.

The mean activity level of the animals as observed by a veterinarian, which was decreased before the administration of SAMe, increased significantly after only one month. It then decreased on average but overall remained above the animals' normal activity. When asked, the owners in turn recognized an appreciable improvement in the activity level of the dogs in the first two weeks of the treatment (38% of the dogs show an improvement), the stimulating effect being more systematically recognized after one month (more than 70% of the dogs show an improvement). SAMe therefore makes it possible to increase the activity level of the animals.

Experiment number 2: Measurement of the effect on the sleeping time of the dogs. See FIG. 2.

On average the sleeping time of the animals tended to normalize, the variations (increase or decrease) observed at the start of the experiment having decreased considerably after two months. SAMe therefore makes it possible to regulate the activity-sleep cycle of the animals.

Experiment number 3: Evaluation of the effect on the anxiety of the dogs. See FIG. 3.

The anxiety of the animals, which can manifest itself in particular by excessive licking of the paws and body, which can itself lead to so-called lick dermatitis, decreased regularly throughout the period over which the animals received SAMe. SAMe therefore makes it possible to reduce the anxiety signs of the animals.

Evaluation by the Owners:

All the owners of the animals studied were satisfied with the treatment at the end of the study and considered the efficacy to be very good. A large majority of the owners noticed a significant improvement in the particular parameters and the general behavior as from the first week of treatment.

Biochemical analyses of blood samples showed that a majority of the dogs had normal values at the start of the experiment which remained within the norms throughout the experiment, demonstrating a very good tolerance to SAMe.

Conclusion:

SAMe administered under the experimental conditions showed a good efficacy in respect of the improvement of certain cognitive disorders in dogs. Furthermore, the owners confirmed that the treatment restored some of the vitality of old dogs.

EXAMPLE 2

Materials and Method

Another study was conducted to show the effect of administering to dogs a nutritional supplement based on S-adenosyl-L-methionine on the behavior and physical signs associated with fear.

The nutritional supplement used in this test consisted of tablets containing 10, 50 or 100 mg of SAMe. It was administered to the animals at a loading dose of 7.5 mg of SAMe per kg of body weight per day in a single daily oral administration for one month, and then at a maintenance dose of 2.5 mg of SAMe per kg of body weight per day in a single daily oral administration for the next two months.

15 dogs aged between 6 months and 15 years are selected with no restrictions on breed, sex or weight. In the two months preceding inclusion in the study, all the dogs presented signs of fear associated either with inhibited behavior or, conversely, with exaggerated responses. This type of problem had to have been identified in the dog for more than two months. The "overall fear score" (sum of the individual scores for the various parameters monitored) recorded at the start of the experiment had to be greater than 7, the parameters observed being as follows:

Pupil dilation. Score: 0=normal, 1=increased, 2=complete.
Trembling. Score: 0=none, 1=slight, 2=pronounced.

Exploration. Score: 0=normal behavior, 1=deteriorated (inhibited, static), 2=highly deteriorated (no exploration or exploratory hyperactivity).

Contact with humans. Score: 0=normal, 1=deteriorated (inhibited), 2=highly deteriorated (no contact or permanent contact with humans).

Mood. Score: 0=calm/joy, 1=deteriorated (loss of vigilance/sadness), 2=highly deteriorated (excitation/depression).

Drool, urine, defecation. Score: 0=no, 3=yes.

Dogs presenting diseases requiring medical treatment (e.g. for problems with arthrosis, kidneys, heart or tumors, infections or infestations) were excluded from the study, as were those which had been treated with psychotropic drugs in the month preceding the study. The administration of psychoactive drugs and/or steroidal or non-steroidal anti-inflammatory drugs was not permitted during the study.

The dogs were examined by an investigator at the start of the experiment and every two weeks for two months, and also one month later. The owners were also asked to give their opinion on the changes observed in the behavior of their dogs.

Result:

It is observed that each parameter monitored during the experiment normalizes during the experiment, with the result that the overall fear score, which reflects the animal's behavior and the physical signs associated with fear, although not falling to zero, nevertheless decreases very substantially (see FIG. 4). This reflects a detectable effect of administering to dogs a nutritional supplement based on S-adenosyl-L-methionine on the behavior and physical signs associated with fear.

EXAMPLE 3

Materials and Method

A study was conducted to show the effects of S-adenosyl-L-methionine on age-related behavioral disorders in cats.

SAMe was administered in the form of tablets containing 90 mg of an S-adenosyl-L-methionine salt (the 1,4-butane-disulfonate).

The tablets were given once a day for a period of 3 consecutive months to comply with the following doses:

Mean dose: 18 (±3.4) mg/kg/d; minimum dose: 12.9 mg/kg/d; maximum dose: 22.5 mg/kg/d.

With no restrictions on breed or species, the study was carried out on 10 cats with ages varying between 12.5 and 19 years which had displayed cognitive disorders for an average of 6 months. These cognitive disorders had been clearly established and observed by their owners and by veterinarians.

These cognitive problems manifested themselves as follows: reduction/loss of interest in the surroundings, withdrawn, less lively, prostration; ambulation; vocalizations, meowing at night; increased sleeping time; decrease in grooming activity; occasional lack of fecal cleanliness.

The blood parameters were analyzed by the veterinarian every month. The owners were also asked to give their opinion on the changes observed in the behavior of their pets.

In this study the term "unchanged" or "normal" means identical to the parameters exhibited by the adult animal in full possession of its faculties.

Experiment number 1: Measurement of the effect of SAMe 1,4-butane-disulfonate on the activity-sleep cycle of the cats. See FIG. 5.

A return to a normal day-night cycle was observed for 7 out of 10 cats in one month. No cat exhibited periods of waking with a start or nightmares in this study. With the help of SAMe some cats slept much better, although they confused day and night. The cats also slept less during the day.

Experiment number 2: Measurement of the effect of SAMe on the elimination behavior of the cats. See FIG. 6.

Cats are normally very clean animals capable of using their litter as from the age of two months. This behavior can change, especially in old cats, which are capable of moving the location of their evacuations generally to soft furnishings. Within the framework of the experiment conducted with SAMe according to the invention, this behavior improved in 2 out of 5 cats, i.e. in 40% of cases.

Experiment number 3: Measurement of the effect of SAMe on the exploratory Behavior of the cats. See FIG. 7.

It was found that the administration of SAMe has a perceptible activating effect as from 15 days of treatment. The cats are more active and they meow to go out. With the help of SAMe the cats are more active and more curious and react better to their surroundings.

Experiment number 4: Ambulation or vocalization behavior.

It was observed that 70% of the cats exhibited ambulation or vocalization periods at the start of the experiment, whereas no cat showed such signs as from the second month. The effect is rapid since only 30% of the cats in the experiment still exhibited ambulation or vocalization periods 15 days after the start of the experiment.

Experiment number 5: Play activity of the cats. See FIG. 8.

SAMe showed a promising net effect on the play activity of the cats after one month. There was a positive result in 7 out of 10 cats at 2 months. With the help of SAMe a majority of the cats regained their liveliness.

Experiment number 6: Interactions/recognition (with/of the owners, other animals). See FIG. 9.

The cats which initially presented an interaction deficit responded rather well (activating effect of the composition). The results are more variable in the cats which manifested hyperattachment.

Experiment number 7: Aggressiveness/irritability of the cats. See FIG. 10.

In three months SAMe made it possible to eliminate 80% (in 4 out of 5 cats) of the manifestations of aggressiveness or irritability encountered in 50% of the old cats in the experiment.

Evaluation by the Owners:

The owners of the animals studied were satisfied with the treatment at the end of the study and all considered the efficacy to be very good. A large majority of the owners noticed a very rapid, significant improvement in the particular parameters and the general behavior as from the first week of treatment.

Biochemical analyses of blood samples showed that a majority of the cats in the experiment had normal values at the start of the experiment which remained within the norms throughout the experiment, demonstrating a very good tolerance to SAMe in cats.

Conclusion:

This study showed that a regular supplementation of old cats with S-adenosyl-L-methionine made it possible to improve and restore a large part of the cats' customary behavior without causing side effects.

EXAMPLE 4

Materials and Method

A randomized double-blind placebo-controlled study was conducted to show the effects of S-adenosyl-L-methionine on the reduced mental capacity of old dogs.

With no restrictions on breed or species, the study was carried out on 36 dogs with an average age greater than 8 years which had displayed one or more behavioral disorders for at least one month. These behavioral disorders had been clearly established and observed by their owners and by veterinarians.

These behavioral disorders manifested themselves as follows: disorientation, decrease in activity, decrease in social interactions, changes in activity-sleep cycle, lack of cleanliness, anxiety.

The dogs were randomly assigned to one of two treatment groups: SAMe or placebo. SAMe (tosylate salt) was administered in the form of tablets once a day for a period of one month to comply with an average dose of 18.5 mg/kg/d.

The dogs were examined by an investigator at the start of the experiment and then at 30 days and 60 days. The owners were also asked to give their opinion on the changes observed in the behavior of their dogs.

The examinations looked at the various behavioral disorders of the animals, which were evaluated on a scale of 0 to 3 according to their intensity, and all the scores were added together to give a "standardized geriatric behavior score" reflecting the severity of the problems observed.

Result:

A significant reduction of the "standardized geriatric behavior score" was observed in both groups over the study period, but the reduction was more significant with SAMe than with placebo (see FIG. 11).

Several dogs in the SAMe group responded to the treatment more favorably than the dogs in the placebo group.

Response to the Treatment at D60

| No. (%) of dogs | No response | Poor response | Good response |
|---|---|---|---|
| SAMe (n = 17) | 6 (35.3%) | 4 (23.5%) | 7 (41.2%) |
| Placebo (n = 19) | 12 (63.2%) | 4 (21%) | 3 (15.8%) | n = number of dogs

The average improvement in terms of activity (57.1%), reactivity (59.5%) and learning behavior, more particularly cleanliness (57.1%), was clinically significant after two months of treatment with SAMe.

A majority of the owners were satisfied with the treatment at the end of the study and they had the impression that their animals were more active and reactive under treatment.

The invention claimed is:

1. A method of reducing the intensity of one or more age-related behavioral changes in a pet, comprising: administering to the pet, in a nutritional supplement, an amount of S-adenosyl-L-methionine or one of its salts effective for reducing the intensity of one or more age-related behavioral changes, the nutritional supplement being administered for a period of time of at least 15 days.

2. The method according to claim 1, wherein the S-adenosyl-L-methionine salt is at least one selected from the group consisting of the salts of S-adenosyl-L-methionine with hydrochloric acid, sulfuric acid, p-toluenesulfonic acid, formic acid, acetic acid, citric acid, tartaric acid and maleic acid, and the double salts of S-adenosyl-L-methionine with said acids.

3. The method according to claim 1 wherein the effective amount of SAMe or one of its salts is between about 1 mg per kg of body weight of the pet per day and about 50 mg per kg of body weight of the pet per day.

4. The method according to claim 3, wherein the effective amount of SAMe or one of its salts is about 7 mg per kg of body weight of the pet per day.

5. The method according to claim 3, wherein the effective amount of SAMe or one of its salts is between about 2.5 and about 20 mg per kg of body weight of the pet per day.

6. The method according to claim 1, wherein the period of time is up to 16 weeks.

7. A method of restoring a behavior of a pet to normal in a pet having one or more age-related behavioral changes, comprising:
administering to the pet, in a nutritional supplement, an amount of S-adenosyl-L-methionine (SAMe) or one of its salts effective for treating the one or more age-related behavioral changes, the nutritional supplement being administered for a period of time of 15 days.

8. The method according to claim 6, wherein the SAMe salt is at least one selected from the group consisting of the salts of SAMe with hydrochloric acid, sulfuric acid, p-toluenesulfonic acid, formic acid, acetic acid, citric acid, tartaric acid, maleic acid and 1,4-butanedisulfonic acid, and the double salts of SAMe with said acids.

9. The method according to claim 6, wherein the effective amount of SAMe or one of its salts is between about 1 mg per kg of body weight of the pet per day and about 50 mg per kg of body weight of the pet per day.

10. The method according to claim 8, wherein the effective amount of SAMe or one of its salts is between about 2.5 and about 20 mg per kg of body weight of the pet per day.

11. The method according to claim 8, wherein the effective amount of SAMe or one of its salts is about 7 mg per kg of body weight of the pet per day.

12. The method according to claim 7, wherein the period of time is up to 16 weeks.

13. A method for the treatment of symptoms of cognitive dysfunction syndrome in a pet, comprising:
administering to the pet, an amount of S-adenosyl-L-methionine (SAMe) or one of its salts effective for treating symptoms of cognitive dysfunction syndrome.

* * * * *